US00PP20432P2

(12) United States Plant Patent
Ault

(10) Patent No.: US PP20,432 P2
(45) Date of Patent: Oct. 20, 2009

(54) ***BAPTISIA* PLANT NAMED 'MIDNIGHT'**

(50) Latin Name: ***Baptisia* hybrid**
Varietal Denomination: Midnight

(75) Inventor: James R. Ault, Libertyville, IL (US)

(73) Assignee: Chicagoland Grows, Glencoe, IL (US)

( * ) Notice: Subject to any disclaimer, the term of this patent is extended or adjusted under 35 U.S.C. 154(b) by 0 days.

(21) Appl. No.: 12/229,873

(22) Filed: Aug. 27, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Susan B McCormick Ewoldt
(74) *Attorney, Agent, or Firm*—Penny J. Aguirre

(57) ABSTRACT

A new cultivar of interspecific *Baptisia*, 'Midnight', characterized by its upright, vase-shaped growth habit with long inflorescences of violet-blue flowers held well above the foliage, its secondary inflorescences that are produced after the primary inflorescences have past peak producing a long blooming period of at least 3 weeks, its lack of foliage on the lower 20 to 40 cm of stem for suitability for planting with other plants, and its adaptability to cultivation in alkaline clay soils.

3 Drawing Sheets

Botanical classification: *Baptisia* hybrid.
Cultivar designation: 'Midnight'.

BACKGROUND OF THE INVENTION

The present invention relates to a new and distinct cultivar of hybrid *Baptisia* plant, botanically known as *Baptisia* 'Midnight' and will be referred to hereafter by its cultivar name, 'Midnight'. The new cultivar represents a new false indigo, an herbaceous perennial grown for landscape use.

The new invention arose from an ongoing breeding program in a dedicated test plot in Glencoe, Ill. There are approximately 17 species of *Baptisia* that are native to North America, many of which have highly ornamental flowers and foliage and excellent adaptability to garden cultivation. The breeding program was established in 1995 with the goal of developing novel interspecific *Baptisia* hybrids with unique and superior garden attributes.

'Midnight' was selected as a single unique plant by the inventor in 2003 in Glencoe, Ill. after evaluating seedlings that derived from open-pollination of an unnamed plant of hybrid *Baptisia* (*Baptisia tinctoria*×*Baptisia alba*) in 1998. The Inventor believes that the pollen parent is an unnamed plant of *Baptisia australis* as it was growing next to the seed parent and because it was the only species utilized in the breeding program with blue-violet flowers.

Asexual reproduction of the new cultivar was first accomplished by stem cuttings in August of 2003 in Glencoe, Ill. by the inventor. The characteristics of this cultivar have been determined to be stable and are reproduced true to type in successive generations.

SUMMARY OF THE INVENTION

The following traits have been repeatedly observed and represent the characteristics of the new cultivar as observed for six years in Glencoe, Ill. These attributes in combination distinguish 'Midnight' from other varieties of *Baptisia* known to the inventor.

1. 'Midnight' initially produces long primary inflorescences (up to 68 cm) and as the primary inflorescences are past peak bloom, shorter secondary inflorescences (up to 10 cm) are produced on lateral stems.
2. 'Midnight' blooms for upward of four weeks, about seven to 10 days longer than most other *Baptisia* known to the inventor. This long bloom period is a result of the bloom sequence of primary and secondary inflorescences.
3. 'Midnight' exhibits an upright, vase-shaped growth habit with long inflorescences of violet-blue flowers held well above the foliage.
4. The stems of 'Midnight' lack foliage on the lower 20 to 40 cm of the stem unlike most *Baptisia* known to the inventor, which makes 'Midnight' suitable for planting close to other plants in the landscape.
5. 'Midnight' is adaptable to cultivation in alkaline clay soils.

In comparison to the female parent, an unnamed plant of *Baptisia tinctoria*×*Baptisia alba,* 'Midnight' has violet-blue flowers whereas the female parent has light yellow flowers. 'Midnight' also has longer inflorescences and is more adaptable to cultivation in alkaline clay soils. In comparison to the presumptive male parent, *Baptisia australis,* 'Midnight' has smaller flowers that are deeper and more violet in color, a more upright and vase shaped habit, produces secondary inflorescences, and bears inflorescences that are held above the foliage. *Baptisia australis* in contrast has a broad rounded habit, larger flowers that are lighter and more blue in color, produces only primary inflorescences, and its inflorescences are held so that at least 50% are hidden in the foliage. 'Midnight' can be compared to *Baptisia australis* 'Big Ben' (not patented) as they both have long inflorescences bearing flowers that are violet-blue in color, however, 'Big Ben' differs from 'Midnight' in having a broad rounded habit, in producing only primary inflorescences, in having a shorter bloom period, and in having its inflorescences hidden at least 50% in the foliage. 'Midnight' can also be compared to *Baptisia* 'Solar Flare' (U.S. Plant patent application Ser. No. 12/229,798), which is similar in producing upright stems without foliage on the lower 20 to 40 cm of the stem and in producing secondary inflorescences. 'Solar Flare' differs in having flowers that mature a yellow-tinged violet color, in having purple tinged stems in the spring, and in having a more broad-spreading round habit.

BRIEF DESCRIPTION OF THE DRAWING

The accompanying colored photographs illustrate the overall appearance and distinct characteristics of the new *Baptisia*. The photographs were taken of plants seven years in age as grown outdoors in a trial plot in Glencoe, Ill.

The photograph in FIG. 1 is a view of a plant of 'Midnight' in bloom and illustrates the plant habit and flowering habit.

Figure 1:
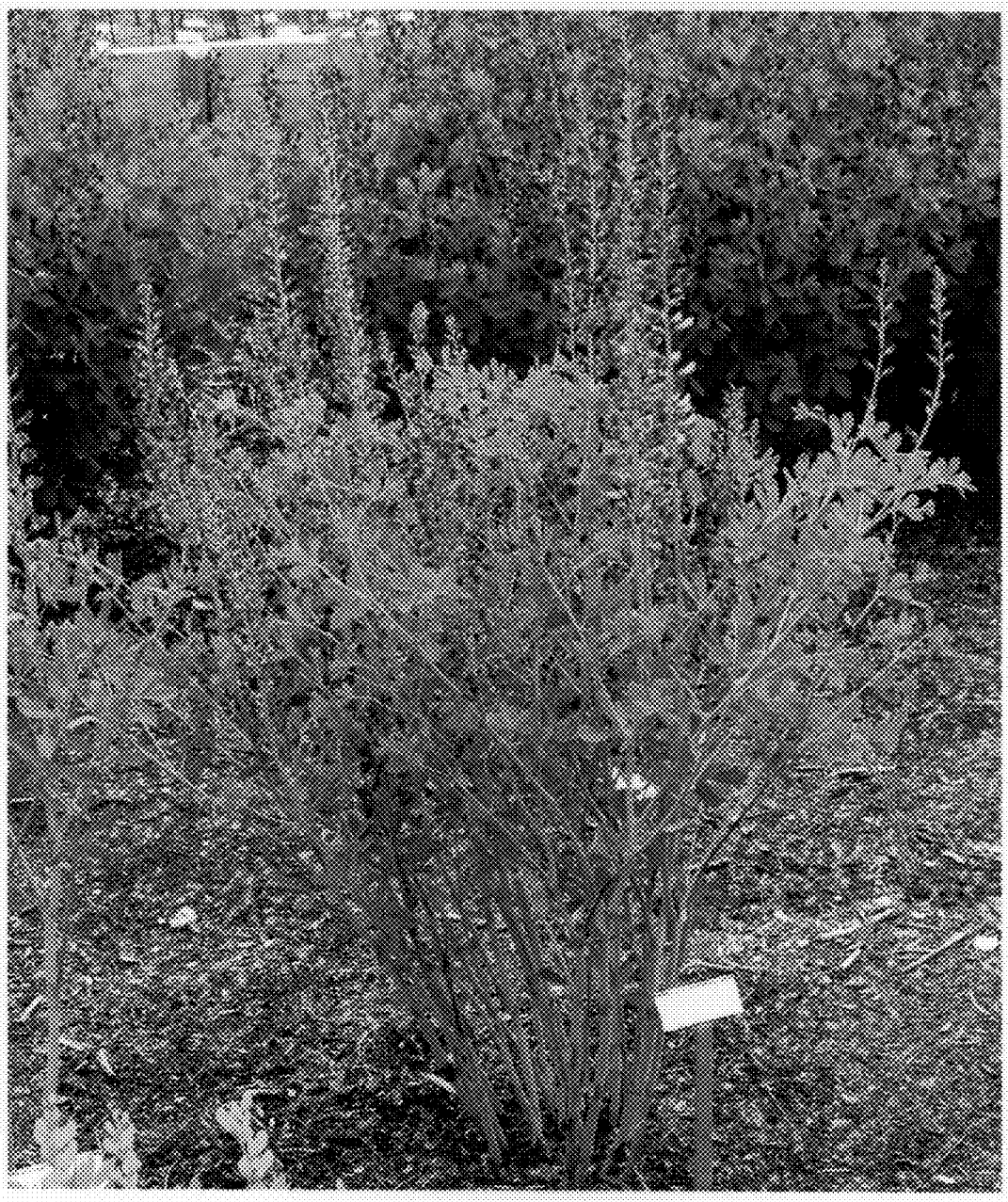
Figure 2:
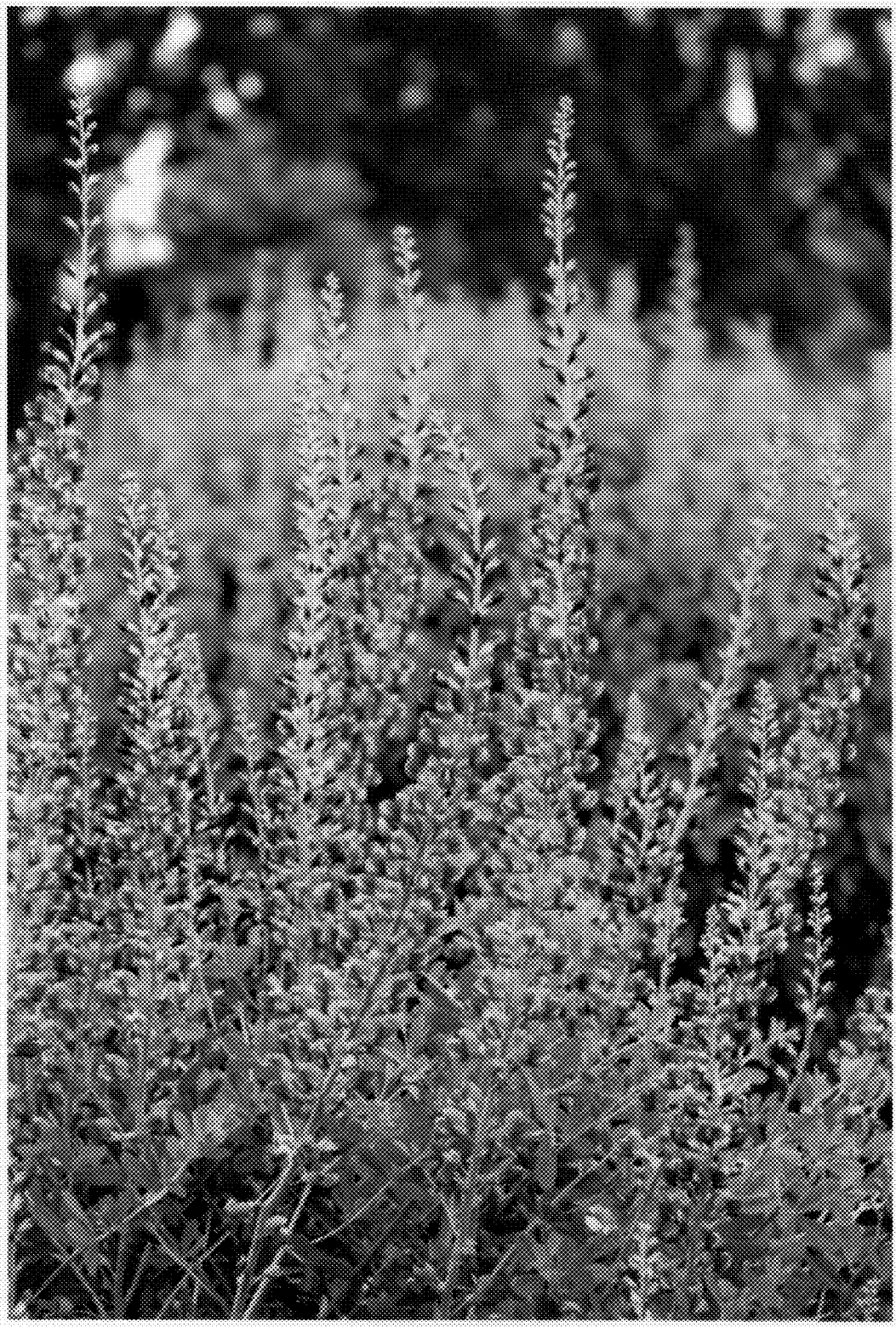

The photograph in FIG. 2 provides of view of both the primary and secondary inflorescences of 'Midnight'.

Figure 3:
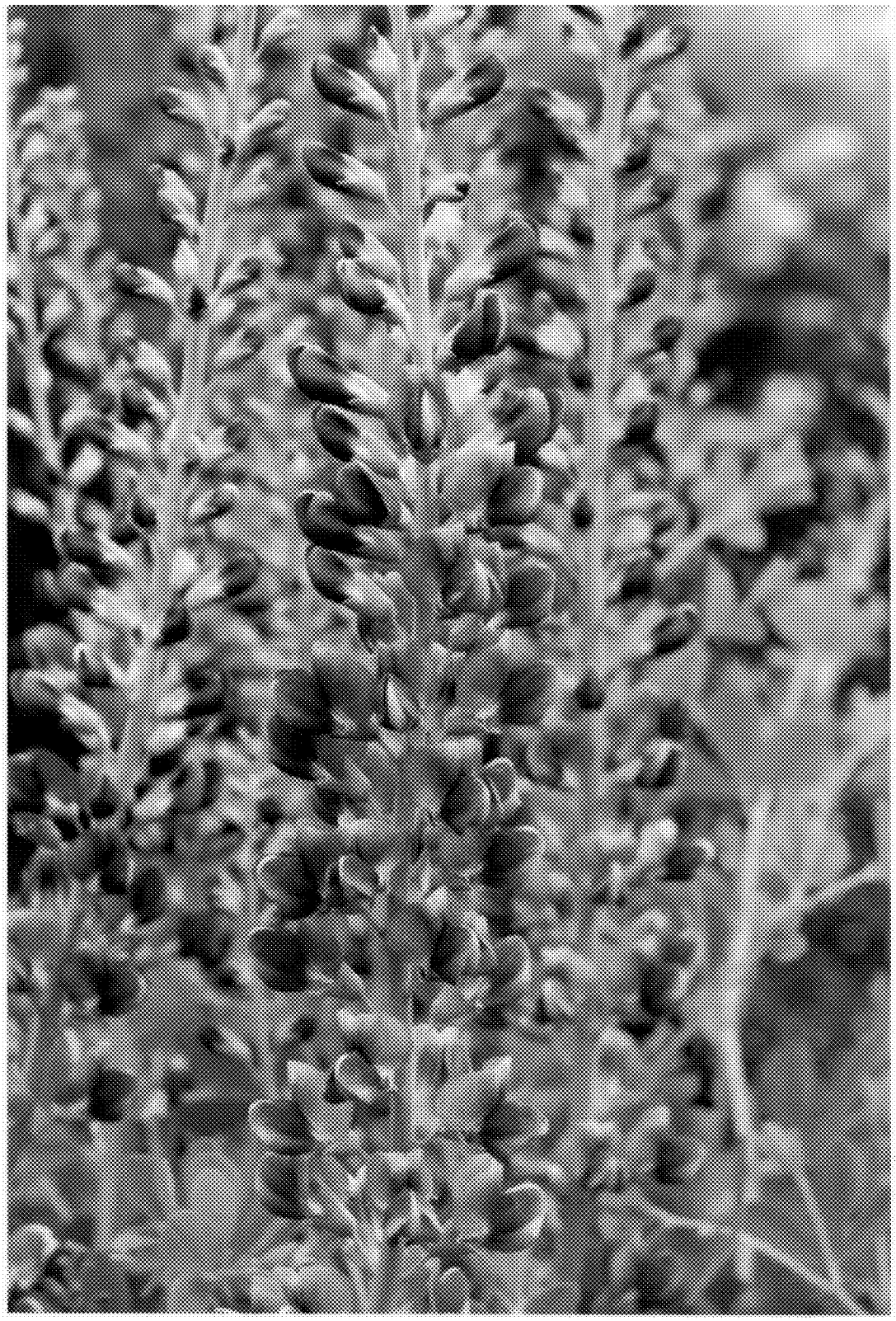

The photograph in FIG. 3 provides a close up view of the flowers of 'Midnight'.

The colors in the photographs are as close as possible with the photographic and printing technology utilized. The color values cited in the detailed botanical description accurately describe the colors of the new *Baptisia*.

DETAILED BOTANICAL DESCRIPTION OF THE PLANT

The following is a detailed description of 7 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—At least 3 weeks in Glencoe, Ill.

*Plant habit.*—Perennial, upright, vase-shaped growth habit with long inflorescences held well above the foliage.

*Height and spread.*—Reaches about 1.2 m in width and 1.25 m in height (in bloom).

*Hardiness.*—U.S.D.A. Zones 4 to 8.

*Culture.*—Prefers well drained to medium moist soils in full sun, tolerant to lean soils and drought, and is adaptable to cultivation in alkaline clay soils.

*Diseases.*—No susceptibility or resistance to diseases has been observed.

*Root description.*—Deep rooted, fibrous.

Growth and propagation:

*Propagation.*—Stem cuttings.

*Growth rate.*—Moderately vigorous relative to other *Baptisia*.

Stem description:

*Branch habit.*—Average of 3 primary branches, typically 2 to 3 secondary branches, and 4 to 5 tertiary branches, primary stems strongly upright, lateral (secondary) stems more lax, resulting in a vase-shaped habit.

*Stem size.*—Reach about 93 cm in length (including raceme), average of 5 mm in width (about 1 cm at base and 2 mm at apex of lateral branches).

*Stem shape.*—Oval.

*Stem color.*—144A.

*Stem surface.*—Hairless, glaucous, finely ribbed.

Foliage description:

*Leaf shape.*—Fan-shaped in overall outline.

*Leaf division.*—3 — palmate.

*Leaf internode.*—Varies from about 12 to 14 cm on basal region of branches and an average of 4.5 cm on secondary branches.

*Leaf size.*—Up to 5 cm in length and 6 cm in width (across all three leaflets) when mature.

*Leaf quantity.*—About 12 to 14 per lateral branch with no foliage on basal 20 to 40 cm of stem.

*Leaflet shape.*—Oblanceolate.

*Leaflet base.*—Attenuate.

*Leaflet apex.*—Rounded to broadly acute.

*Leaflet venation.*—Pinnate pattern, not conspicuous, color matches leaflet color on the upper and lower surface with the mid rib of lower surface 144B.

*Leaflet margins.*—Entire.

*Leaf attachment.*—Petiolate.

*Leaf arrangement.*—Alternate.

*Leaflet surface.*—Slightly glaucous on upper surface, glaucous on lower surface.

*Leaflet color.*—Newly expanded; upper and lower surface 144A to 137B, mature; upper and lower surface 137A with coating of 189A.

*Leaflet size.*—Up to 5 cm in length, up to about 2 cm in width.

*Petioles.*—Average of 1.2 cm in length and 2 mm in width, clasping to stem at mature nodes, between 144A and 144B in color, surface is hairless and satiny.

*Stipules.*—Lanceolate in shape, base is truncate to stem, apex is narrowly acute to acuminate, average of 1 cm in length and 5 mm in width but varies from minute on newly formed leaves to 2.2 cm in length and 8 mm in width on basal nodes, 137A in color on upper and lower surface.

Flower description:

*Inflorescence type.*—Terminal and axillary racemes of papilionaceous flowers, blooms from the base to the apex.

*Inflorescence size.*—Primary (terminal) inflorescences up to 68 cm in length and 6 cm in width, secondary (lateral) inflorescences are up to 10 cm in length.

*Lastingness of inflorescence.*—Primary inflorescences last 13 to 16 days, lateral inflorescences last 5 to 7 days.

*Blooming period.*—Three plus weeks from early to late June in Glencoe, Ill.

*Flower size.*—About 2.3 cm in length and about 2.0 cm in width.

*Flower fragrance* .—None.

*Flower number.*—About 80 to 90 on terminals, about 15 to 20 on axillary branches.

*Peduncle.*—Oval in shape, up to 72 cm in length and ranges from 1.0 cm in width at the base of the inflorescence to 2 mm in width at the apex, 144A in color with coating of 191A, surface is hairless, glaucous, and finely ribbed, flower internode length is an average of 1 cm.

*Petiole.*—About 5 mm in length, about 1.5 mm in width, oval in shape, 144A in color, glaucous surface.

*Flower buds.*—Reniform, about 2 cm in length and 7 mm in width, bicolor 150B to 150C in color with a center region of 93A, calyx portion same as open flowers.

*Flower type.*—Papilionaceous, held at about a 45° angle.

*Calyx.*—Campanulate, about 8 mm in length and 5 mm in diameter, surface is slightly glaucous, 144A to 144B in color, persistent.

*Sepals.*—5, fused with the exception of apex of each, free portion is triangular in shape 4 mm in width and 3 mm in depth with an acute apex, 144A in color.

*Corolla features.*—Papilionaceous (4 segments) with a keel, an inner lip and 2 lateral wings, the inner lip; comprised of two lobes that are folded around stamens and pistil, lobes are reniform in shape, about 1.9 cm in length and 8 mm in width, rounded apex, color is 150D with a blush of 150C towards apex (both surfaces) lateral wings; loosely surround inner lip, oblong in shape, about 1.8 cm in length and 9 mm in width, rounded apex, color is 93A with a streak of 93D on the upper margin and a base of 150D, keel; reflexed, orbicular in shape with cordate apex, about 1.8 cm in length and 2 cm width, color is 93B with veins of 93A and a base of 150D (both surfaces), all segments; glabrous in texture, entire margin. base is rounded with a short attenuated section on keel and oblique with an attenuated section on other segments.

*Receptacle.*—Disk-shaped, gelatinous, 144A in color, about 3 mm in diameter and 1.2 mm in depth.

Reproductive organs:

*Gynoecium.*—1 Pistil, about 1.6 cm in length and 1.5 mm in width; style is 8 mm in length, <1 mm in width, and 143D in color; stigma minute, too small to color read; Ovary is superior with a stipe, 143C in color, 5 mm in length and 1.5 mm in width; stipe is 138D in color, 3 mm in length and <1 mm in width.

*Androcoecium.*—10 stamens, not united, 1.9 cm in length and 1 mm in width; filament is 1.8 cm in length, 1 mm in width and 145C in color; anther is dorsifixed, 1 mm in length and <1 mm in width and completely covered by pollen, pollen is abundant and 17A in color.

*Fruit and seed.*—An inflated pod, technically a legume, globose but slightly oblong in shape, average of 1.5 cm in length and 8 mm in width; each with a beak about 5 mm in length, emerges green, 144B to 144C and matures in August to 202A suffused with 202B, walls about 1.5 mm in thickness and woody at maturity, seed; average of 2 per fruit (open-pollinated), 200A to 200B in color, oval with the hilum side more or less straight, seed compressed to flattish, about 4 mm long×3 mm wide×1.3 mm in thickness.

It is claimed:

1. A new and distinct cultivar of *Baptisia* plant named 'Midnight' as herein illustrated and described.

* * * * *